United States Patent
Reinke et al.

(10) Patent No.: US 7,167,759 B2
(45) Date of Patent: Jan. 23, 2007

(54) ELECTRODE LINE

(75) Inventors: Heinrich Reinke, Baiersdorf-Hagenau (DE); Max Schaldach, deceased, late of Erlangen (DE); by Max Schaldach, Jr., legal representative, Berlin (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 496 days.

(21) Appl. No.: 10/115,356

(22) Filed: Apr. 3, 2002

(65) Prior Publication Data

US 2002/0147412 A1 Oct. 10, 2002

(30) Foreign Application Priority Data

Apr. 5, 2001 (DE) ................. 101 18 797

(51) Int. Cl.
*A61N 1/00* (2006.01)
(52) U.S. Cl. .................................... 607/116
(58) Field of Classification Search ............... 600/146, 600/381; 607/116–125
See application file for complete search history.

(56) References Cited

U.S. PATENT DOCUMENTS

| | | | |
|---|---|---|---|
| 4,753,223 A | 6/1988 | Bremer | |
| 5,415,633 A | 5/1995 | Lazarus | |
| 5,419,312 A | 5/1995 | Arenberg | |
| 5,423,807 A * | 6/1995 | Milder | ............ 606/20 |
| 5,429,131 A | 7/1995 | Scheinman | |
| 5,435,314 A * | 7/1995 | Dias | ............ 600/463 |
| 5,824,031 A | 10/1998 | Crookston | |
| 5,835,453 A | 11/1998 | Wynne | |
| 5,843,153 A | 12/1998 | Johnston | |
| 6,048,307 A | 4/2000 | Gruendl | |
| 6,083,170 A | 7/2000 | Ben-Haim | |
| 6,129,672 A | 10/2000 | Seward | |
| 6,468,203 B1 * | 10/2002 | Belson | ............ 600/146 |
| 6,605,084 B1 * | 8/2003 | Acker et al. | ............ 606/28 |
| 6,610,007 B1 * | 8/2003 | Belson et al. | ............ 600/146 |
| 2005/0085693 A1 * | 4/2005 | Belson et al. | ............ 600/146 |

FOREIGN PATENT DOCUMENTS

| | | |
|---|---|---|
| DE | 195 46 941 A1 | 6/1997 |
| DE | 198 07 487 A1 | 8/1999 |
| DE | 200 10 369 U1 | 9/2000 |
| FR | 2732225 A1 | 10/1996 |
| WO | WO 99/17929 A1 | 4/1999 |
| WO | WO 00/07641 A2 | 2/2000 |
| WO | WO 00/28911 A1 | 5/2000 |
| WO | WO 00/53077 A2 | 9/2000 |

* cited by examiner

*Primary Examiner*—George Manuel
(74) *Attorney, Agent, or Firm*—Hahn Loeser & Parks LLP

(57) ABSTRACT

An electrode line, in particular for an implantable electro-stimulation device, which is adapted for insertion into body vessels such as heart chambers or blood vessels, comprising electrodes for the stimulation of body tissue, a longitudinal axis and a distal end, wherein there is provided at least one structural element (2) in the region of the distal end, which has an electrostrictive polymer and which can be connected to a voltage source by way of at least one electrical feed line (3) and which is adapted to change its shape when an electrical voltage is applied.

26 Claims, 2 Drawing Sheets

ELECTRODE LINE

The invention concerns an electrode line, in particular for an implantable electrostimulation device, which is adapted for insertion into body tissue such as heart chambers or blood vessels, and has electrodes for the stimulation of body tissue, a longitudinal axis and a distal end.

BACKGROUND OF THE INVENTION

Electrode lines are preferably used to electrically stimulate surrounding body tissue or record electrical signals. They are used in particular also in the region of the coronary vessels or veins in order to control heart contraction. For that purpose, the requirement is that the electrode can be introduced into the selected vessel. That should be implemented with minimum invasion in order to save the patient major stress levels. If the electrode is to be disposed in the coronary sinus at the left atrium or in one of the adjoining veins at the left ventricle, then access takes place in the following fashion: the electrode is firstly passed through a transvenous or venous access, of comparatively large volume, to the right atrium. Thereupon it has to describe virtually a right angle in order to pass into the coronary sinus. If the electrode is to be pushed deeper into the coronary sinus and if further bending movements are to be implemented, a guide wire is provided which provides for displaceability of the electrode. A further requirement lies in steerability of the electrode line in order to guide the electrode line through curved or branched cavities.

U.S. Pat. No. 6,083,170 to Ben-Haim describes a flexible elongate probe having an orientation mechanism which flexes the distal end of the probe in dependence on control signals. Piezoelectric crystals or shape memory alloys are proposed as controllable flexing elements. Electrode lines for the stimulation of tissue, in particular the myocardium, are however intended to be permanently implanted. The control mechanisms which are operated with piezoelectric crystals or shape memory alloys however are usually not sufficiently stable in the long term. The permanently implanted electrodes have to withstand a large number of flexing movements which are caused by variations which are specific to the body, such as for example for the heart beat. In that respect the piezoelectric crystals and shape memory alloys have a tendency to work through the electrode sheath of the electrode line after a certain number of passive flexing movements.

Therefore the object of the present invention is to provide an electrode line of the kind set forth in the opening part of this specification, which can be permanently implanted and which has a suitable control mechanism.

SUMMARY OF THE INVENTION

The object of the present invention is attained by the subject of accompanying claim 1. The electrode line of claim 1 is characterized by a structural element in the region of the distal end, which structural element has an electrostrictive polymer and which can be connected by way of at least one electrical line to a voltage source and is adapted to change its shape when an electrical voltage is applied. Electrostrictive polymers have the property of changing their shape, in particular contracting, when a voltage is applied thereto. Therefore it is possible to move the distal end of the electrode line by means of the structural element with the electrostrictive polymer. That represents a control mechanism with which the operation of introducing the electrode line is made easier and which replaces a separate guide wire. The electrode line can therefore be of a smaller diameter than one which has a lumen for a separate guide wire. Electrostrictive polymers also have the property of being flexible. They can withstand a multiplicity of passive flexing movements without becoming brittle or damaging the adjoining electrode or the sheath thereof. Therefore the electrode according to the invention is suitable for permanent implantation.

The structural element is preferably arranged with respect to the electrodes in such a way that a curvature of the longitudinal axis of the electrode line, in the region of the distal end, can be changed by applying an electrical voltage. By virtue of flexing of the distal region of the electrode line with respect to the longitudinal axis thereof, it is possible to change the direction in which it is passed through cavities specific to the body such as arteries or veins. In particular the operation of introducing the electrode line into a cavity which is disposed laterally with respect to the longitudinal axis thereof, such as the opening to a vein, is made easier.

The electrode line preferably includes a plurality of structural elements which can be connected to the voltage source independently of each other and which are actuable by the voltage source. In that way it is possible for the distal end of the electrode line to be curved in different directions with respect to the longitudinal axis. Each individual structural element produces a specific deformation of the electrode line, depending on the respective arrangement and position. A desired shape can thus be imparted to the electrode line by simultaneous actuation of the structural elements. The distal end of the electrode line can be more easily oriented in a desired direction. Two of the structural elements are preferably arranged, with respect to a cross-section of the electrode line, on oppositely disposed sides of the cross-section. The arrangement of the two structural elements has to be such that selective application of electrical voltage to one of the structural elements causes a curvature of the electrode line in a different direction from application of the voltage to the respective other element. The deflection of the electrode tip or the distal end of the electrode line can thus be variably adjusted. In particular, it is possible for the distal end to be curved in opposite directions with respect to the longitudinal axis. The variability of possible deflection movements of the distal end can be further increased by virtue of using a plurality of the structural elements which respectively occupy a sector of the cross-section of the electrode line. The sectors respectively form different surface portions of the cross-section of the electrode line, which for example come about by virtue of the fact that the cross-section is divided into a plurality of portions by means of straight lines passing through the longitudinal axis of the electrode line. The structural elements within the sectors of the cross-section, by virtue of their changes in shape, generally being contraction changes, cause a curvature of the electrode line, which is dependent on the position of the sector. In that way it is possible for curvatures of the distal end of the electrode line to be precisely adjusted.

The electrode line can be designed in such a way that it is pre-curved, that is to say it entails a curvature in the region of the structural elements even when no voltage is applied to the structural elements. The structural elements are preferably designed in such a way that they increase or reduce the pre-curvature of the electrode line. For that purpose, there are provided two structural elements, wherein a respective one of the structural elements increases the curvature or reduces the curvature. The structural element which reduces the curvature is preferably designed in such a way that it can eliminate the curvature entirely. The advantage of this pre-curved electrode line is that it can be curved to a greater degree than an electrode line with identical structural elements, which is not pre-curved.

A further preferred electrode line is one which, in the region of the electrostrictive structural elements, is of structure and/or shape which facilitates deflection (flexing) of the electrode line in that region. A suitably advantageous structure for the electrode line can include for example a helical electrical feed line for the (stimulation or defibrillation) electrode, the turns of which are spaced from each other in the region of the electrostrictive structural elements in order to enhance the flexibility of the electrode line. Alternatively or additionally, the electrode line may have notches to increase flexibility in the region of an inside radius of the intended bend or alternatively or additionally in the region of an outside radius of the bend to be produced by the electrostrictive structural elements.

The electrical feed line for connecting the electrostrictive polymer to the voltage source preferably extends from the proximal end of the electrode line to the structural element. The voltage source can therefore be placed at a separate location from the distal end of the electrode line. In order to limit the number of electrical feed lines, it is possible to use an electrical feed line for the (stimulation or defibrillation) electrode as the electrical feed line for the electrostrictive structural elements. It is particular preferred if that electrical feed line is adapted to make available a common reference potential for a plurality of electrostrictive structural elements.

The electrode line preferably includes a flexible electrode sheath which encases the electrode line in the region of the distal end, with the structural element being integrated into the electrode sheath. The electrostrictive polymer of the structural element is a flexible material which can be in the form of a component part of the electrode sheath, without causing any problem. Preferably, an electrostrictive material with a very low level of conductivity is used in order to prevent a flow of current into surrounding tissue. The same applies to the flexible electrode sheath used. Integration of the structural element into the electrode sheath permits miniaturization of the electrode line. That is required in particular if the electrode line is to be guided into small cavities, for example vessels of small diameter.

Preferably the structural element is disposed in the region of the distal end of the electrode line and beside the longitudinal axis thereof. Arranging the structural element beside the longitudinal axis affords the advantage that the curvature of the distal end with respect to the longitudinal axis is already very great, even in the event of slight deformation of the structural element.

Embodiments of the present invention are described hereinafter with reference to the accompanying drawings.

It may also be advantageous for a group of the structural elements to be adapted to be actuatable in group-wise manner. For that purpose the structural elements of one of the groups are connected for example by way of a common electrical feed line to the voltage source. At the same time that reduces the number of electrical feed lines. When a signal is applied to the common electrical feed line by the voltage source, that signal goes to each of the electrical feed lines and causes simultaneous deformation of the structural elements. A group of the structural elements can be selected in such a way that it only includes structural elements which are spaced from each other in the direction of the longitudinal axis. By virtue of simultaneous actuation, the electrode line is simultaneously bent at different locations on its longitudinal axis. A further possible selection of structural elements of a group can include those structural elements which are arranged in different sectors of the cross-section of the electrode line. If that group of structural elements is simultaneously actuated, then the electrode line is simultaneously deformed in different sectors in the peripheral direction of the electrode line.

DETAILED DESCRIPTION OF THE INVENTION

Figure 1:
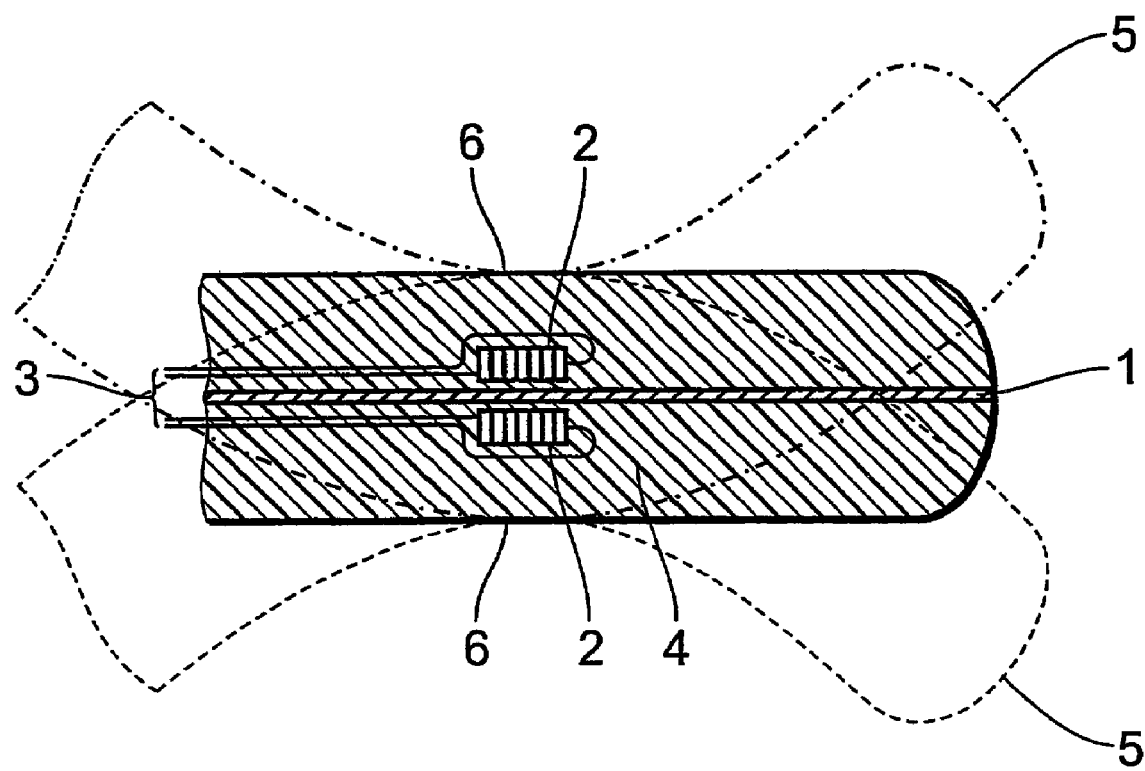
FIG. 1 shows an electrode line in the region of the distal end in accordance with a first embodiment of the present invention.

FIG. 1 shows a side view in section of an electrode line. The electrode 1 extends along the longitudinal axis of the electrode line and is surrounded by a flexible electrode sheath 4. The broken lines show the outline of the electrode line when it has been curved. This will be discussed in greater detail hereinafter. Two structural elements 2 are integrated in the electrode sheath 4 on opposite sides of the electrode 1. The structural elements 2 are each connected to respective ones of two electrical feed lines 3 which lead to the proximal end (not shown) of the electrode line and are there connected to a voltage source. The two structural elements 2 can be actuated separately. The structural elements 2 each have a respective electrostrictive polymer which changes its shape when a voltage is applied. In the preferred embodiment the application of a voltage to one of the two structural elements 2 causes them to be contracted in the direction of the longitudinal axis. By virtue of the interconnected embedding of the structural elements 2 in the elastic electrode sheath 4 contraction in the region of the structural element 2 causes the electrode line generally to be deformed. The end of the electrode line is curved towards the structural element 2 with respect to the longitudinal axis. The curvature 6 in the region of the structural element 2 is at its maximum. This embodiment has the advantage that the distal end of the electrode 2 can be curved in mutually opposite directions.

Figure 2:
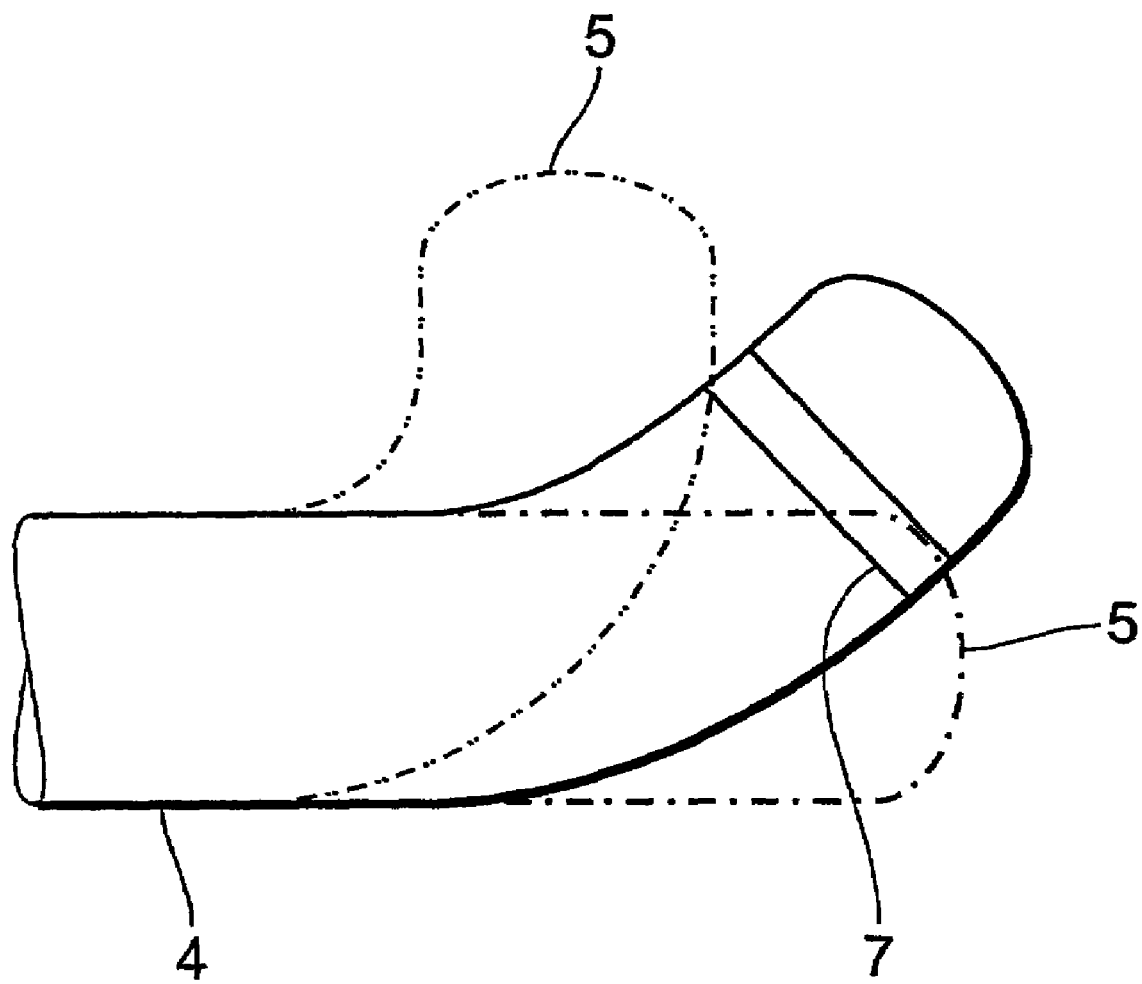
FIG. 2 shows an electrode line in the region of the distal end in accordance with a second embodiment of the present invention.

FIG. 2 also shows a distal end of an electrode line in accordance with a second embodiment. The arrangement of the electrode 1, the structural elements 2 and the electrical feed lines 3 in the interior of the electrode line is identical to the arrangement shown in FIG. 1 and is therefore not illustrated. Reference 4 again shows the flexible electrode sheath, with no voltage being applied to the structural elements. The electrode sheath 4 or the distal end of the electrode is curved in that condition in contrast to the electrode line shown in FIG. 1. Reference 5 again shows the outline of the electrode line, which can occur when a voltage is applied to the structural elements 2. The distal end is deformed by the structural elements 2 to such an extent that it involves no curvature with respect to the longitudinal axis of the electrode. The curvature can further be increased in such a way that the distal end is inclined through an angle of 90° with respect to the longitudinal axis of the electrode line.

FIG. 2 also shows a ring electrode 7 which can usually be connected by way of an electrical line to a heart pacemaker or another therapy unit and serves for example for stimulating or registering electrical signals in the heart tissue.

The invention claimed is:

1. A pre-bent electrode line, having a limited capacity to constrict in any allowable direction, for an implantable electrostimulation device for insertion into a body vessel, said electrode line comprising:
   at least one electrode for stimulation or sensing of body tissue;
   a longitudinal axis;
   a distal end,
      wherein said electrode line is of a partially-bent configuration at least in a region of said distal end when no voltage is applied to structural elements within said electrode line;
      a first limited number of electrostrictive polymer structural elements, having only a limited capacity to constrict, on a first side of said electrode line;
      a second limited number of electrostrictive polymer structural elements, having only a limited capacity to constrict, on a second side of said electrode line, said second side being directly opposite of said first side; and
   a voltage source connected to said electrostrictive polymer structural elements,
      wherein application of a first voltage from said voltage source to said first limited number of electrostrictive polymer structural elements causes said electrode line to straighten from said partially-bent configuration to a straight configuration,
      and wherein application of a second voltage from said voltage source to said second limited number of electrostrictive polymer structural elements causes said electrode line to bend from said partially-bent configuration to a bent configuration having a tighter bending radius than said partially-bent configuration,
      and wherein said electrode line relaxes to said partially-bent configuration from said straight configuration when said first voltage from said voltage source is removed from said first limited number of electrostrictive polymer structural elements,
      and wherein said electrode line relaxes to said partially-bent configuration from said bent configuration when said second voltage from said voltage source is removed from said second limited number of electrostrictive polymer structural elements.

2. The electrode line as set forth in claim 1, wherein the structural elements are adapted and are arranged with respect to the rest of the electrodes such that a curvature of the longitudinal axis of the electrode line, in the region of the distal end, can be varied by applying an electrical voltage.

3. The electrode line of claim 2, wherein said structural elements can be connected to the voltage source and actuated by the voltage source independently of each other.

4. The electrode line of claim 3, wherein
   two of the structural elements are disposed on opposite sides of a cross-section of the electrode line so that the selective application of electrical voltage to one of the structural elements causes curvature of the electrode line in a direction different from application of the voltage to the respective other structural element.

5. The electrode line of claim 4, wherein
   each of a plurality of the structural elements occupies a respective sector in the peripheral direction of the electrode line with respect to the cross-section thereof.

6. The electrode line of claim 5, further comprising:
   a flexible sheath encasing the electrodes, wherein the structural elements are integrated into the electrode sheath.

7. The electrode line of claim 6, wherein
   the structural elements are arranged beside the longitudinal axis in the region of the distal end.

8. The electrode line of claim 3, wherein
   the structural elements can be connected to the voltage source so as to be actuable in groups by the voltage source.

9. The electrode line of claim 8, further comprising:
   an electrical feed line for the at least one electrode which is the electrical feed line of one or more structural elements.

10. The electrode line of claim 8, wherein
    a group of the co-actuable structural elements comprises structural elements which are spaced from each other along the longitudinal axis.

11. The electrode line of claim 8, wherein
    a group of the co-actuable structural elements comprises structural elements arranged in different radial sectors.

12. The electrode line of claim 8, wherein
    selected structural elements of one of the groups are co-actuable by virtue of being connectable to the voltage source by way of a common electrical line.

13. The electrode line of claim 3, wherein
    each of the structural elements occupies a respective sector in the peripheral direction of the electrode line with respect to a cross-section thereof.

14. The electrode line of claim 1 further comprising electrical feed lines, wherein
    the electrical feed lines extend from a proximal end of the electrode line to the respective structural elements.

15. The electrode line of claim 1, further comprising:
    a flexible sheath encasing the electrodes, wherein the structural elements are integrated into the electrode sheath.

16. The electrode line of claim 1, wherein
    the structural elements are arranged beside the longitudinal axis in the region of the distal end.

17. The electrode line of claim 1, further comprising
    a configuration which increases the flexibility of the electrode line in the region of the electrostrictive structural elements and/or a structure which increases said flexibility, in the region of the electrostrictive structural elements.

18. The electrode line of claim 1, wherein
    said structural elements can be connected to the voltage source and actuated by the voltage source independently of each other.

19. The electrode line of claim 18, wherein
    two of the structural elements are disposed on opposite sides of a cross-section of the electrode line so that the selective application of electrical voltage to one of the structural elements causes curvature of the electrode line in a direction different from application of the voltage to the respective other structural element.

20. The electrode line of claim 19, wherein
    each of the structural elements occupies a respective sector in the peripheral direction of the electrode line with respect to the cross-section thereof.

21. The electrode line of claim 18, wherein
each of the structural elements occupies a respective sector in the peripheral direction of the electrode line with respect to a cross-section thereof.

22. The electrode line of claim 18, wherein
the structural elements can be connected to the voltage source so as to be actuable in groups by the voltage source.

23. The electrode line of claim 22, further comprising:
an electrical feed line for the at feast one electrode which is the electrical feed line of one or more structural elements.

24. The electrode line of claim 22, wherein
a group of the co-actuable structural elements comprises structural elements which are spaced from each other along the longitudinal axis.

25. The electrode line of claim 22, wherein
a group of the co-actuable structural elements comprises structural elements arranged in different radial sectors.

26. The electrode line of claim 22, wherein
selected structural elements of one of the groups are co-actuable by virtue of being connectable to the voltage source by way of a common electrical line.

* * * * *